US 10,842,362 B2

(12) United States Patent
Matsuura

(10) Patent No.: US 10,842,362 B2
(45) Date of Patent: Nov. 24, 2020

(54) BENDABLE TUBE SEGMENT, BENDABLE TUBE AND INSERTION DEVICE

(71) Applicant: OLYMPUS CORPORATION, Tokyo (JP)

(72) Inventor: Wataru Matsuura, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 70 days.

(21) Appl. No.: 15/430,753

(22) Filed: Feb. 13, 2017

(65) Prior Publication Data

US 2017/0150879 A1 Jun. 1, 2017

Related U.S. Application Data

(63) Continuation of application No. PCT/JP2015/071988, filed on Aug. 3, 2015.

(30) Foreign Application Priority Data

Sep. 30, 2014 (JP) .................... 2014-201267

(51) Int. Cl.
  *A61B 1/005* (2006.01)
  *A61M 25/01* (2006.01)
  (Continued)

(52) U.S. Cl.
  CPC ............ *A61B 1/0055* (2013.01); *A61B 1/008* (2013.01); *A61B 1/0051* (2013.01);
  (Continued)

(58) Field of Classification Search
  CPC .......... A61M 25/0133; A61M 25/0136; A61M 25/0138; A61M 25/0141; A61M 25/0144; A61M 25/0147; A61M 2025/0161; A61B 1/005; A61B 1/0051; A61B 1/0052; A61B 1/0053; A61B 1/0055; A61B 1/0056; A61B 1/0057; A61B 1/0058; A61B 1/008; A61B 1/01; A61B 1/00071; A61B 1/00078;
  (Continued)

(56) References Cited

U.S. PATENT DOCUMENTS

2013/0041224 A1\* 2/2013 Okaniwa .............. A61B 1/0055
  600/142

FOREIGN PATENT DOCUMENTS

JP  S62-281918 A  12/1987
JP  S62281918 A  * 12/1987 ........... A61B 1/0055
  (Continued)

OTHER PUBLICATIONS

International Search Report dated Oct. 20, 2015 issued in PCT/JP2015/071988.
(Continued)

*Primary Examiner* — Ryan N Henderson
(74) *Attorney, Agent, or Firm* — Scully, Scott, Murphy & Presser, P.C.

(57) ABSTRACT

A bendable tube segment includes annular members and wire insertion portions. The wire insertion portion is provided on the annular member to shift by a third angle, which is an obtuse angle smaller than a first angle, in the same direction as the first angle. The wire insertion portion is provided on the annular member to shift by a fourth angle, which is an acute angle larger than a second angle, in the same direction as the second angle.

12 Claims, 9 Drawing Sheets

(51) Int. Cl.
*A61B 1/00* (2006.01)
*A61B 1/008* (2006.01)
*A61B 1/018* (2006.01)
*A61B 1/273* (2006.01)
*A61B 17/00* (2006.01)

(52) U.S. Cl.
CPC ........ *A61B 1/0057* (2013.01); *A61B 1/00071* (2013.01); *A61B 1/018* (2013.01); *A61B 1/273* (2013.01); *A61M 25/0147* (2013.01); *A61B 2017/00318* (2013.01); *A61B 2017/00323* (2013.01)

(58) Field of Classification Search
CPC .... A61B 2017/003; A61B 2017/00305; A61B 2017/00309; A61B 2017/00314; A61B 2017/00318; A61B 2017/00323; A61B 2017/00327
See application file for complete search history.

(56) References Cited

FOREIGN PATENT DOCUMENTS

| JP | H03-218723 A | | 9/1991 | |
|---|---|---|---|---|
| JP | 2004-141366 A | | 5/2004 | |
| JP | 2004141366 A | * | 5/2004 | ........... A61B 1/0055 |
| JP | 2007-252447 A | | 10/2007 | |
| JP | 2010-201011 A | | 9/2010 | |
| JP | 2010201011 A | * | 9/2010 | ........... A61B 1/0055 |
| WO | WO 2011/111258 A1 | | 9/2011 | |
| WO | WO 2011/136115 A1 | | 11/2011 | |

OTHER PUBLICATIONS

English translation of International Preliminary Report on Patentability dated Apr. 13, 2017 together with the Written Opinion received in related International Application No. PCT/JP2015/071988.

* cited by examiner

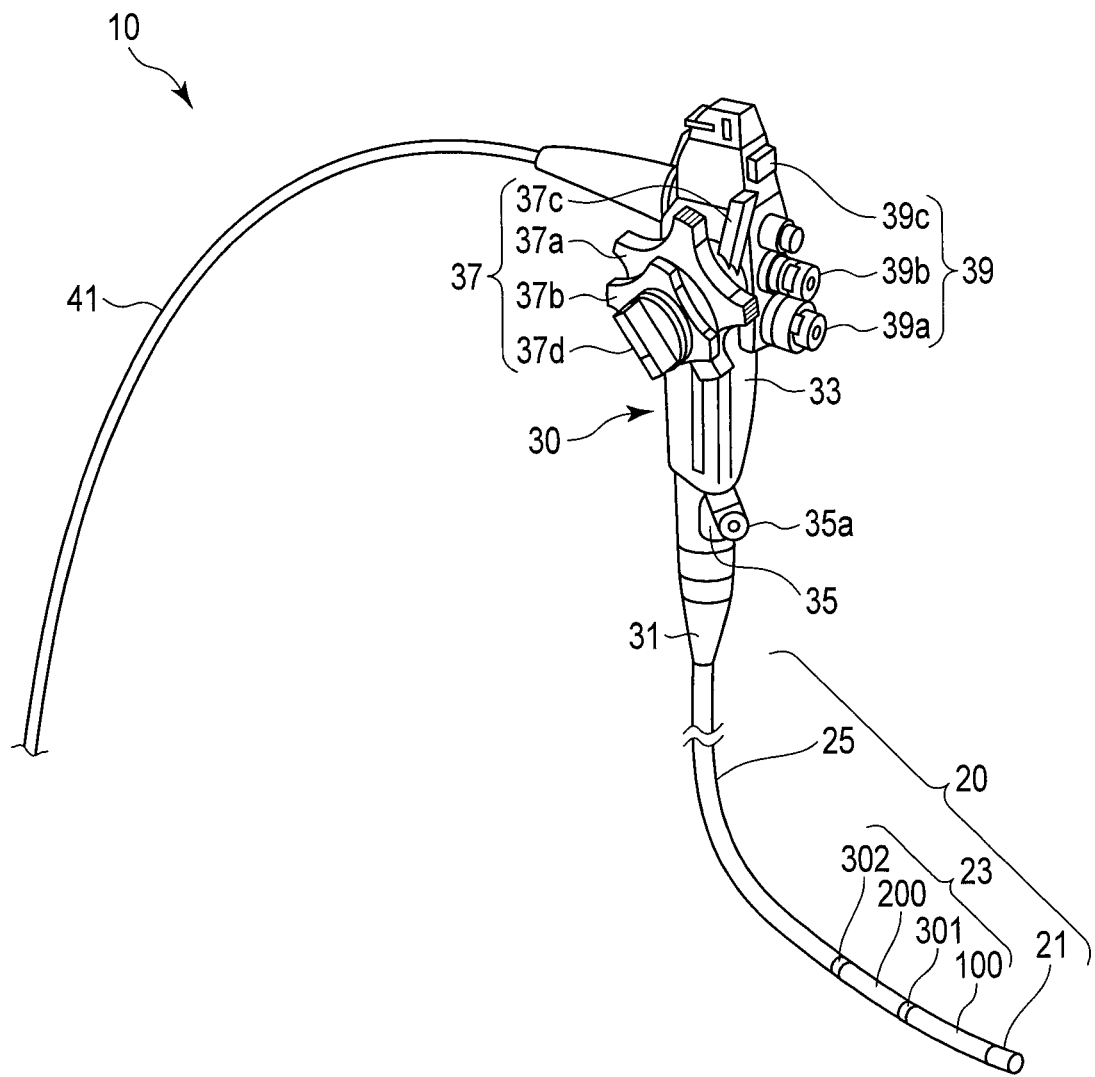
F I G. 1

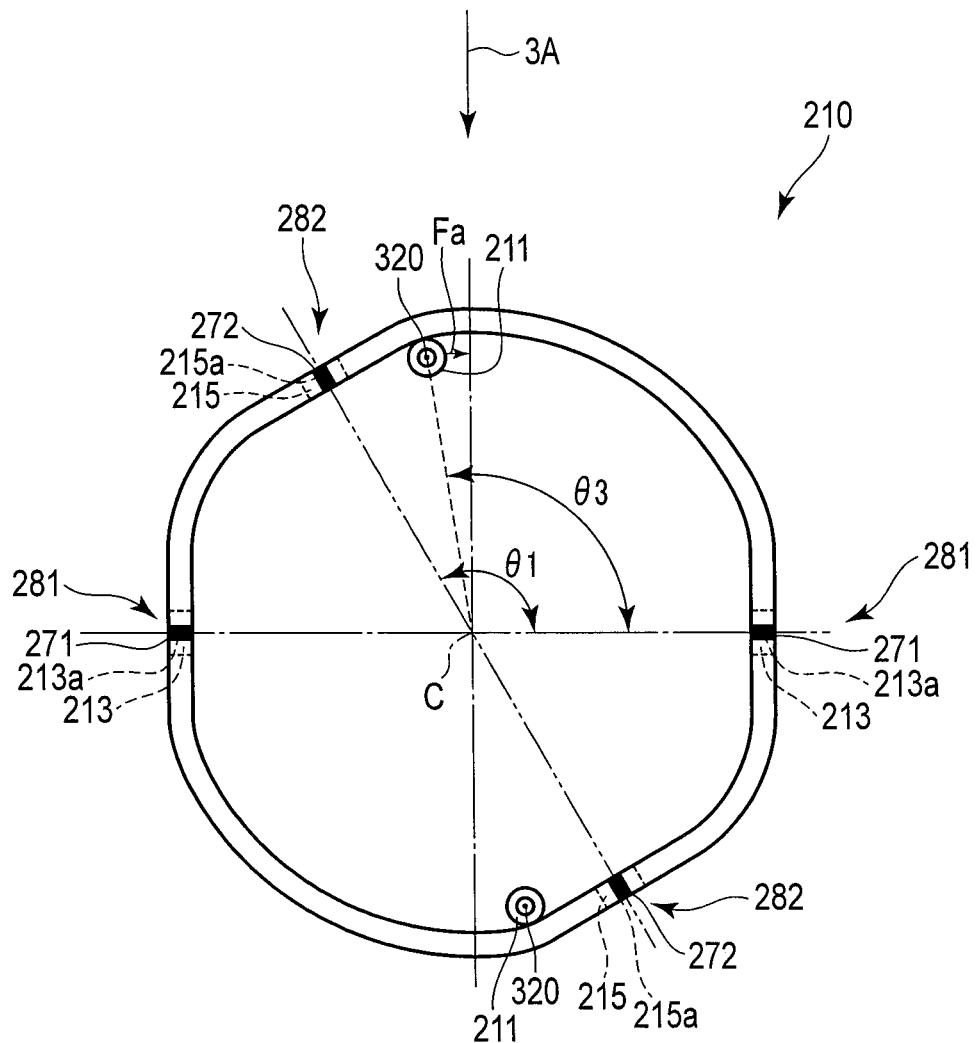
F I G. 3B

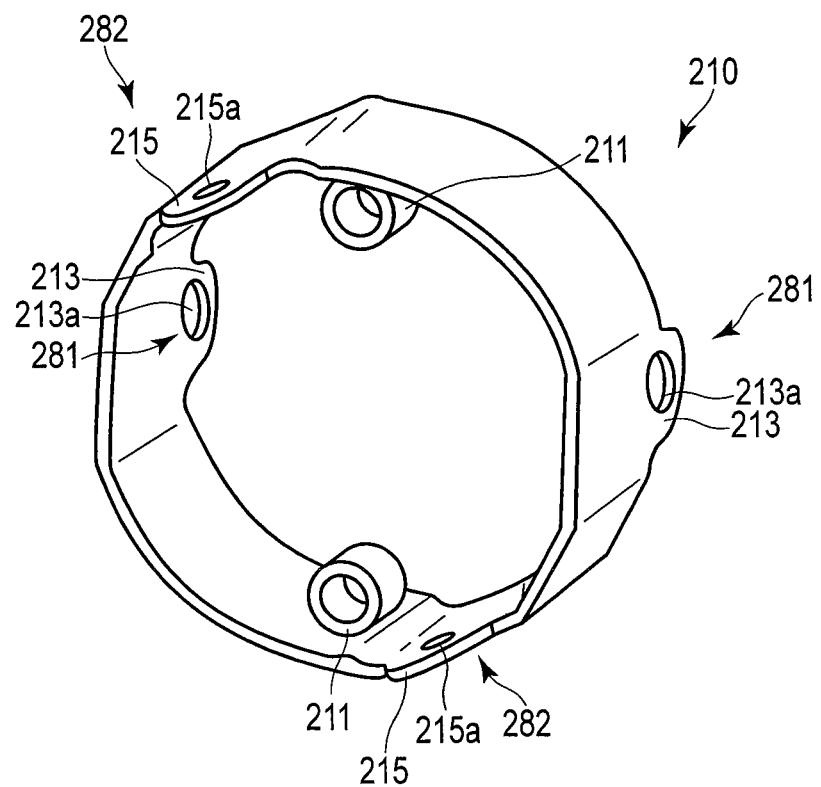
F I G. 4A

BENDABLE TUBE SEGMENT, BENDABLE TUBE AND INSERTION DEVICE

CROSS-REFERENCE TO RELATED APPLICATIONS

This application is a Continuation Application of PCT Application No. PCT/JP2015/071988, filed Aug. 3, 2015 and based upon and claiming the benefit of priority from prior Japanese Patent Application No. 2014-201267, filed Sep. 30, 2014, the entire contents of all of which are incorporated herein by reference.

BACKGROUND OF THE INVENTION

1. Field of the Invention

The present invention relates to a bendable tube segment, a bendable tube and an insertion device.

2. Description of the Related Art

The bendable tube disclosed in, for example, International Publication No. 2011-136115 includes an active bendable portion and a passive bendable portion connected to a proximal end portion of the active bendable portion. The active bendable portion is actively bent in, for example, four directions of up, down, right and left directions and a combined direction of the four directions by drawing operation wire. The active bendable portion is passively bent by receiving an external force. The passive bendable portion is passively bent in, for example, four directions of up, down, right and left directions and a combined direction of the four directions. In addition to these directions, the bending directions of the passive bendable portion are determined in detail as disclosed in International Publication No. 2011-136115, and the passive bendable portion is curved in six directions of up and down directions, first diagonal directions and second diagonal directions and a combined direction of the six directions so as to obtain an effective bend during the procedure.

BRIEF SUMMARY OF THE INVENTION

According to one aspect of the present invention, a bendable tube segment which is bendable by connecting a plurality of annular members provided along a central axis extending in a longitudinal direction by a plurality of joint portions including a rotation axis orthogonal to the central axis, comprises a first annular member included in the annular members; a second annular member included in the annular members, the rotation axis being shifted by a predetermined angle from the first annular member; a third annular member included in the annular members, the rotation axis being shifted by another predetermined angle from the first annular member and the second annular member; a pair of first wire insertion portions provided on an inner surface of the first annular member to shift at an angle from a straight line orthogonal to the rotation axis on which the first annular member rotates, a pair of operation wires being inserted through each of the first wire insertion portions to move in an axial direction of the operation wires; and a pair of second wire insertion portions provided on an inner surface of the second annular member to shift at an angle from a straight line orthogonal to the rotation axis on which the second annular member rotates, the pair of operation wires being inserted through each of the second wire insertion portions to move in the axial direction of the operation wires.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic diagram of an endoscope according to one embodiment of the present invention.

FIG. 3B is a diagram showing a relationship in position between each structural member of a first annular member shown in FIG. 3A and a rotation axis thereof.

FIG. 4A is a perspective view of the first annular member shown in FIGS. 3A and 3B.

DETAILED DESCRIPTION OF THE INVENTION

Figure 2A:
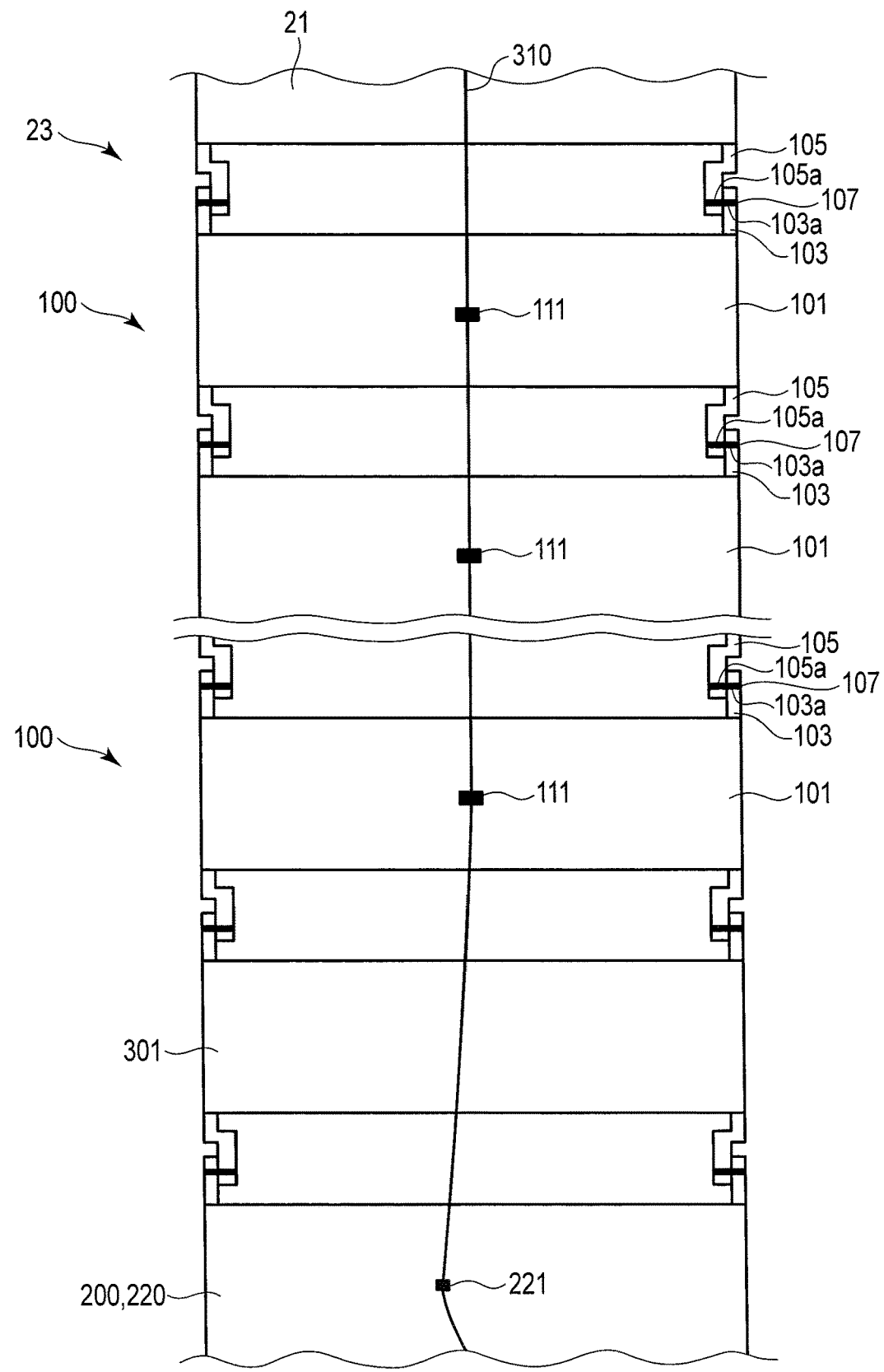
FIG. 2A is a diagram illustrating a connecting structure of a first bendable tube.

An embodiment of the present invention will be described below with reference to the drawings.

One Embodiment

Configuration

One embodiment will be described with reference to FIGS. 1, 2A, 2B, 3A, 3B, 3C, 3D, 4A and 4B. FIG. 3B is a diagram showing a relationship in position between each structural member (projection portions 213 and 215, a wire insertion portion 211, etc.) and a rotation axis, and does not show a specific section of the annular member 210. This is true of an annular member 230 shown in FIG. 3C and an annular member 220 shown in FIG. 3D. In some of the figures, some of the members are not shown for clarification.

Endoscope 10

An endoscope 10 functions as, for example, an insertion device that is inserted into a lumen of a body cavity and the like. The endoscope 10 of the present embodiment is, for example, a direct cholangioscope that is inserted directly into a bile duct.

The endoscope 10 includes a long insertion portion 20 that is inserted into a lumen of a patient's body cavity and an operation portion 30 connected to a proximal end portion of the insertion portion 20 to operate the endoscope 10.

Insertion Portion 20

The insertion portion 20 includes a distal hard portion 21, a bendable tube 23 and a flexible tube portion 25 along an axis extending in the longitudinal direction of the insertion portion 20 in the order from a distal end portion of the insertion portion 20 to the proximal end portion of the insertion portion 20. A proximal end portion of the distal hard portion 21 is connected to a distal end portion of the bendable tube 23, and a proximal end portion of the bendable tube 23 is connected to a distal end portion of the flexible tube portion 25. The configuration of the bendable tube 23 will specifically be described later.

Operation Portion 30

The operation portion 30 includes a main body portion 31 from which the flexible tube portion 25 extends, a grasping portion 33 connected to a proximal end portion of the main body portion 31 and grasped by an operator who operates the endoscope 10, and a universal cord 41 connected to the grasping portion 33.

Grasping Portion 33

The grasping portion 33 includes a treatment instrument insertion portion 35 provided to insert a treatment instrument into the endoscope 10, a bending operation portion 37 to bend the bendable tube 23, and a switch portion 39. The treatment instrument insertion portion 35 is provided on a distal end portion side of the grasping portion 33, and the bending operation portion 37 and switch portion 39 are provided on the proximal end portion side of grasping portion 33.

Bending Operation Portion 37

The bending operation portion 37 includes a first operation knob 37a to bend a first bendable tube 100 of the bendable tube 23 up and down, for example and a second operation knob 37b to bend a second bendable tube 200 of the bendable tube 23 up and down, for example. The bending operation portion 37 also includes a first fixing knob 37c to fix a position of the first bendable tube 100 and a second fixing knob 37d to fix a position of the second bendable tube 200.

Switch Portion 39

The switch portion 39 includes a suction switch 39a, an air/water feed switch 39b, and a variety of switches 39c for endoscope imaging. The suction switch 39a, air/water feed switch 39b and switches 39c are operated by a hand of the operator when the grasping portion 33 is grasped by the operator.

Universal Cord 41

The universal cord 41 extends from a side surface of the grasping portion 33. The universal cord 41 is connected to a control device (not shown) and the like.

Bendable Tube 23

The bendable tube 23 includes the first bendable tube 100 provided on the distal end portion side of the insertion portion 20 and the second bendable tube 200 provided on the proximal end portion side of the insertion portion 20. The distal end portion of the first bendable tube 100 is connected to the distal hard portion 21, a proximal end portion of the first bendable tube 100 is connected to a distal end portion of the second bendable tube 200 through a first mouthpiece portion 301, and a proximal end portion of the second bendable tube 200 is connected to the distal end portion of the flexible tube portion 25 through a second mouthpiece portion 302. The first mouthpiece portion 301 can be included in the first bendable tube 100 or the second bendable tube 200. The second mouthpiece portion 302 can be included in the second bendable tube 200. The first and second mouthpiece portions 301 and 302 are, for example, annular members.

The first bendable tube 100 actively bends greatly in, e.g. an up-and-down direction by drawing first operation wire 310 (see FIG. 2A) as the first operation knob 37a is operated. A distal end portion of the first operation wire 310 is fixed onto, e.g. an inner surface of the distal hard portion 21. The distal end portion of the first operation wire 310 may be fixed onto an inner surface of an annular member 101 provided at a most distal end of the first bendable tube 100. A proximal end portion of the first operation wire 310 is inserted through the second bendable tube 200 and the flexible tube portion 25 and connected to the first operation knob 37a. The first bendable tube 100 can be bent passively in an up-and-down direction. The configuration of the first bendable tube 100 will specifically be described later.

The second bendable tube 200 actively bends small in, e.g. an up-and-down direction by drawing second operation wire 320 (see FIG. 3A) as the second operation knob 37b is operated. A distal end portion of the second operation wire 320 is fixed onto, e.g. the inner surface of the mouthpiece portion 301. The distal end portion of the second operation wire 320 may be fixed onto an inner surface of an annular member 210 provided at a most distal end of the second bendable tube 200. A proximal end portion of the second operation wire 320 is inserted through the flexible tube portion 25 and connected to the second operation knob 37b. The second bendable tube 200 can be bent passively in an up-and-down direction. The second bendable tube 200 can be bent passively in first and second diagonal directions in addition to the up-and-down direction. The configuration of the second bendable tube 200 will specifically be described later.

Configuration of First Bendable Tube 100

Figure 2B:
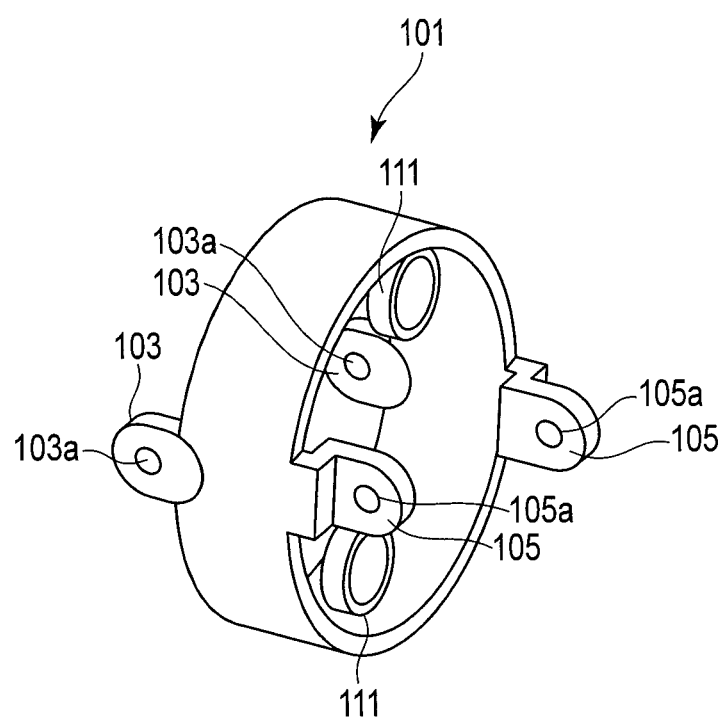
FIG. 2B is a perspective view of an annular member of the first bendable tube.
Figure 3A:
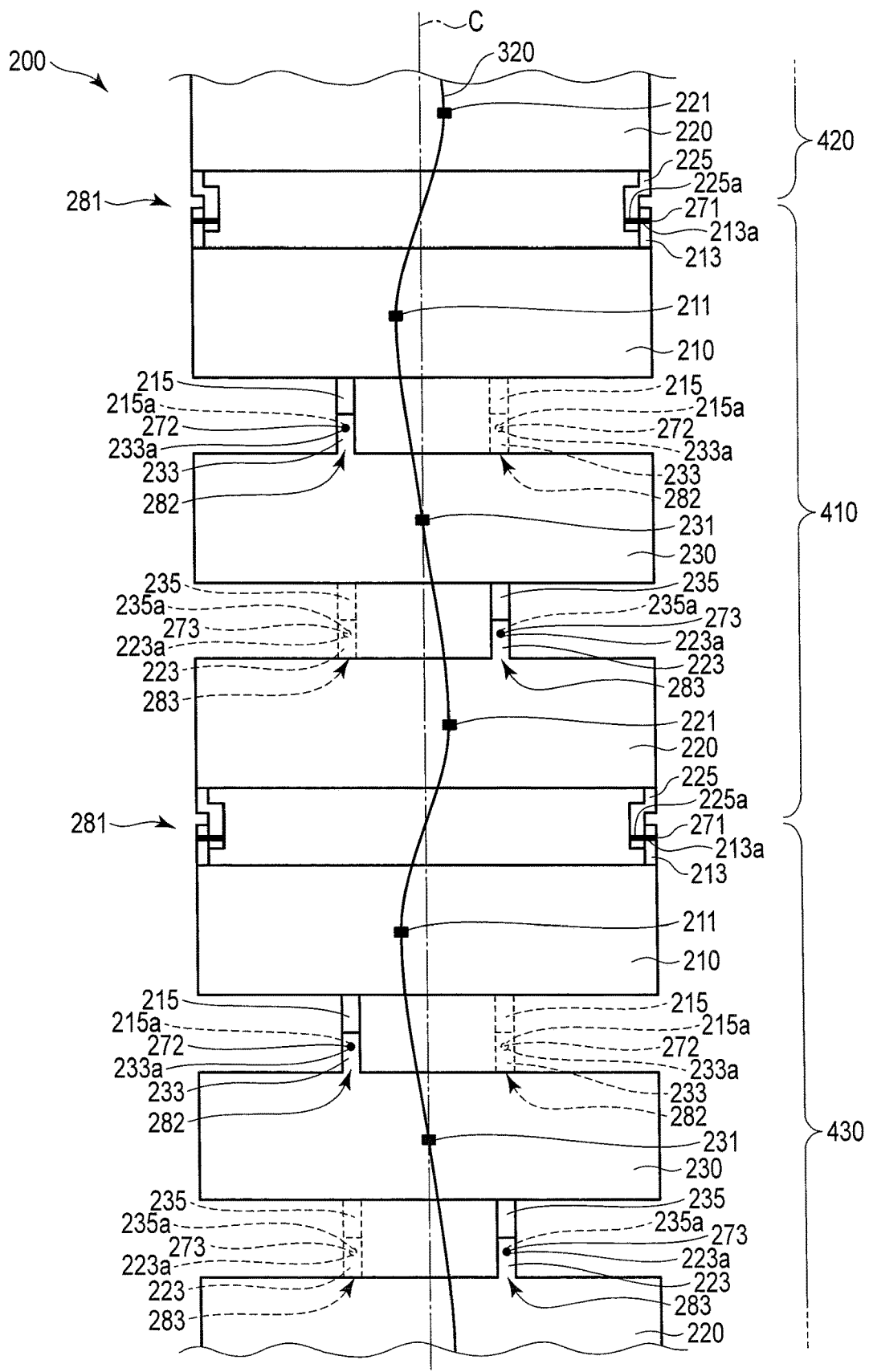
FIG. 3A is a diagram illustrating a connecting structure of a second bendable tube and a meandering state of second operation wire.

As shown in FIGS. 2A and 2B, the first bendable tube 100 is configured by arranging a plurality of substantially cylindrical (annular) annular members 101 along the longitudinal direction of the insertion portion 20. Adjacent annular members 101 are rotatably connected to each other by a connecting portion described later. If the annular members 101 are rotatably connected to each other, the first bendable tube 100 is formed such that it can be bent (rotated) as described above. The annular members 101 are, for example, joint rings. These annular members 101 and first mouthpiece portion 301 function as bendable tube segments by which the first bendable tube 100 is configured.

The annular member 101 as shown in FIG. 2B is formed of a hard material such as metal. The annular member 101 is molded by, e.g. pressing or cutting a metal thin plate.

As shown in FIG. 2B, a pair of projection portions 103 is formed on a front end portion side (left side of FIG. 2B) of the annular members 101. The projection portions 103 are front side hinge mounts. The projection portions 103 are portions of the annular member 101 which are projected toward the front and formed in a planar state. The front means the distal end portion side of the first bendable tube 100. Each projection portion 103 has a through hole portion 103a that is formed through the projection portion 103 in a thickness direction of the projection portion 103. The two projection portions 103 are separated by approximately 180 degrees from each other in a circumferential direction of the annular member 101.

A pair of projection portions 105 is formed on the rear end portion side (right side of FIG. 2B) of the annular members 101. The projection portions 105 are rear side hinge mounts. The projection portions 105 are portions of the annular member 101 which are projected toward the rear and formed in a planar state. The rear means the proximal end portion side of the first bendable tube 100. Each projection portion 105 has a step. The step has a thickness that is substantially the same as that of each of the projection portions 103. Each projection portion 105 has a through hole portion 105a that is formed through the projection portion 105 in a thickness direction of the projection portion 105. The two projection portions 105 are separated by approximately 180 degrees from each other in the circumferential direction.

The two projection portions 103 on the front side are formed in the same position as the two projection portions 105 on the rear side in the circumferential direction.

With respect to the projection portion 105 of the annular member 101 provided alongside the distal hard portion 21 and the projection portion 103 of the annular member 101 provided alongside the second bendable tube 200, for example, the projection portion 103 is stacked on the projection portion 105 in such a manner that the through hole portion 103a communicates with the through hole portion 105a. In this state, a rivet 107 that is a rotation member (axis) is inserted into each of the through hole portions 103a and 105a. Accordingly, the annular member 101 alongside the flexible tube portion 25 and the annular member 101 alongside the distal hard portion 21 are connected to each other through the rivet 107 and supported rotatably around the rivet 107 as a center. Between the projection portions 103 and 105, therefore, a support shaft portion which includes the rivet 107 that is a rotation support shaft is formed.

In other words, the projection portions 103 and 105 and rivet 107 function as a connecting portion that connects the annular member 101 alongside the flexible tube 25 and the annular member 101 alongside the distal hard portion 21. The projection portions 103 and 105 and rivet 107 function as a joint portion including a first up-and-down rotation axis of the first bendable tube 100 that bends in an up-and-down direction, and are located in, for example, the right-and-left direction of the up-and-left and right-and-left directions on a cross section of the annular member 101. The first up-and-down rotation axis is orthogonal to an axis extending along a central axis of the bendable tube 23, that is the longitudinal axis of the insertion portion 20.

As shown in FIG. 2B, Each annular member 101 includes a pair of wire insertion portions 111 which is provided on the inner surface thereof, and through which the first operation wire 310 is inserted. The wire insertion portions 111 are separated by approximately 180 degrees from each other in the circumferential direction. The wire insertion portions 111 are separated by approximately 90 degrees from the projection portions 103 and 105 in the circumferential direction. The wire insertion portions ill are members that receive the first operation wire 310. Thus, the first operation wire 310 is inserted through the wire insertion portions 111 and moves forward and backward therein in the axial direction of the first operation wire 310. In this case, the wire insertion portions 111 have only to be shaped like a cylinder such that the first operation wire 310 can be inserted through the wire insertion portions 111.

These wire insertion portions 111 may be members different from the annular member 101, may be formed of a hard material such as metal and may be fixed to the inner surface of the annular member 101 by, for example, welding or brazing, not shown. As shown in FIG. 2A, the wire insertion portions 111 are formed on the same straight line in the longitudinal direction of the first bendable tube 100.

The wire insertion portions 111 can be shaped by pressing, cutting and bending part of a peripheral wall portion of the annular member 101 from the outer surface of the annular member 101 toward the inner surface thereof and thus projecting and raising the part.

With the foregoing configuration, the first bendable tube 100 is provided on the distal end portion side of the central axis of the bendable tube 23. In the first bendable tube 100, the annular members 101 are provided along the central axis of the bendable tube 23 extending in the longitudinal direction, that is an axis extending along the longitudinal axis of the insertion portion 20, and connected by a plurality of joint portions including the rotation axis that is perpendicular to the central axis. Thus, the annular members 101 are connected to each other and the first bendable tube 100 can be bent. The first bendable tube 100 actively bends in the up-and-down direction by drawing the first operation wire 310 as the first operation knob 37a is operated, and passively bends in the up-and-down direction.

If the first bendable tube 100 is bent, the distal hard portion 21 varies in its position and direction. Then, an observation target is illuminated with illumination light and captured within an observation field. The observation target is, for example, an affected area and a pathological area in a subject (e.g. body cavity).

Configuration of Second Bendable Tube 200

As shown in FIGS. 3A, 3B, 3C and 3D, the second bendable tube 200 includes three annular members 210, 220 and 230 of different types as one unit. As shown in FIG. 3A, in one unit, for example, the first annular member 210, third annular member 230 and second annular member 220 are arranged, for example, in the order presented along the longitudinal direction of the insertion portion 20 from the distal end portion of the second bendable tube 20 toward the proximal end portion of the second bendable tube 200. In the longitudinal direction of the insertion portion 20, the annular member 220 is arranged between the annular members 210 and 230. These annular members 210, 230 and 220 and the first and second mouthpiece portions 301 and 302 function as bendable tube segments by which the second bendable tube 200 is configured. The second bendable tube 200 is provided on the proximal end portion side of the central axis of the bendable tube 23 and connected to the proximal end portion of the first bendable tube 100, and thus can be bent. In the second bendable tube 200, the annular members 210, 230 and 220 are arranged along the central axis of the bendable tube 23 extending in the longitudinal direction, that is along an axis extending along the longitudinal axis of the insertion portion 20, and connected by a plurality of joint portions including the rotation axis that is orthogonal to the central axis. Accordingly, the annular members 210, 230 and 220 are connected to each other and the second bendable tube 200 can be bent.

For example, each of the annular members 210, 230 and 220 functions as one bendable tube segment, and the second bendable tube 200 includes a plurality of bendable tube segments. In this case, the bendable tube segments are arranged along the central axis of the bendable tube segments and connected to each other. The details of these bendable tube segments will be described later. If the bendable tube segments are connected to each other along the central axis C, the second bendable tube 200 is formed.

As shown in FIG. 3A, in one bendable tube segment 410, the annular member 210 is rotatably connected to the annular member 230 by a connecting portion described later, and the annular member 230 is rotatably connected to the annular member 220 by a connecting portion described later. In the bendable tube segment 410, the annular member 210 is rotatably connected to the annular member 220 of another bendable tube segment 420 by a connecting portion described later, the annular member 220 is provided more forward than the bendable tube segment 410 and is adjacent to the bendable tube segment 410. In the bendable tube segment 410, the annular member 220 is rotatably connected to the annular member 210 of another bendable tube segment 430 by a connecting portion described later, the annular member 210 is provided more backward than the bendable tube segment 410 and is adjacent to the bendable tube segment 410. In the second bendable tube 200, the annular members are arranged in the order of 210, 230, 220, 210, 230, 220 as presented here. The rotation axis of the annular member 220 is shifted by a predetermined angle from that of the annular member 210, the details of which will be described later. The rotation axis of the annular member 230 is shifted by another predetermined angle from those of the annular members 210 and 220.

As shown in FIGS. 1 and 2A, in the second bendable tube 200, the annular member 210 of the bendable tube segment provided at the most distal end is connected to the first mouthpiece portion 301. The annular member 220 of the bendable tube segment provided at the most proximal end is connected to the second mouthpiece portion 302 (see FIG. 1).

Configuration Common to Annular Members 210, 220 and 230

The configuration common to the annular members 210, 220 and 230 will be described. As one example, the configuration will be described here using the annular member 210 shown in FIGS. 3A and 3B. The configuration of the annular member 210 is substantially the same as that of the annular member 101 shown in FIG. 2B. The annular members 210, 220 and 230 are of substantially the same.

The annular member 210 as shown in FIGS. 3B and 4A is formed of a hard material such as metal. The annular member 210 is formed by, for example, pressing or cutting a metal thin plate.

As shown in FIG. 3A, a pair of projection portions 213 are provided on a front end portion side (shown in the upper part of FIG. 3A) of the annular member 210. The projection portions 213 are front side hinge mounts. The projection portions 213 are portions of the annular member 210 which are projected toward the front and formed in a planar state. The front means the distal end portion side of the second bendable tube 200. Each projection portion 213 has a through hole portion 213a that is formed through the projection portion 213 in a thickness direction of the projection portion 213. As shown in FIGS. 3B and 4A, the two projection portions 213 are separated by approximately 180 degrees from each other in a circumferential direction of the annular member 210. The shape of the projection portions 213 is substantially the same as that of the projection portions 103.

As shown in FIG. 3A, a pair of projection portions 215 are provided on the rear end portion side (shown in the lower part of FIG. 3A) of the annular member 210. The projection portions 215 are rear side hinge mounts. The projection portions 215 are portions of the annular member 210 which are projected toward the rear and formed in a planar state. The rear means the proximal end side of the second bendable tube 200. Each projection portion 215 has a step. The step has a thickness that is substantially the same as that of each of the projection portions 213. Each projection portion 215 has a through hole portion 215a that is formed through the projection portion 215 in a thickness direction of the projection portion 215. As shown in FIGS. 3B and 4A, the two projection portions 215 are separated by approximately 180 degrees from each other in the circumferential direction. The shape of the projection portions 215 is substantially the same as that of the projection portions 105. When the projection portions 215 are viewed from arrow 3A shown in FIG. 3B, the projection portion 215 close to arrow 3A (the projection portion 215 shown in the upper part of FIG. 3B) is indicated by a solid line in FIG. 3A, and the projection portion 215 far from arrow 3A (the projection portion 215 shown in the lower part of FIG. 3B) is indicated by a dotted line in FIG. 3A. In other words, the projection portion 215 indicated by the solid line in FIG. 3A is provided on an upper surface side of the annular member 210 and the projection portion 215 indicated by the dotted line in FIG. 3A is provided on a lower surface side of the annular member 210.

Unlike in the annular member 101, in the annular member 210, the positions of the front two projection portions 213 are different from those of the rear two projection portions 215 in the circumferential direction as shown in FIGS. 3A, 3B and 4A.

The annular member 210 includes a pair of wire insertion portions 211 formed on an inner surface thereof, through which the second operation wire 320 is inserted. The wire insertion portions 211 are separated by approximately 180 degrees from each other in the circumferential direction of the annular member 210. The wire insertion portions 211 are members that receive the second operation wire 320. Thus, the second operation wire 320 is inserted through the wire insertion portions 211 and moves forward and backward therein in the axial direction of the second operation wire 320. In this case, the wire insertion portions 211 have only to be shaped like a cylinder such that the second operation wire 320 can be inserted through the wire insertion portions 211.

These wire insertion portions 211 are formed of a hard material such as metal and may be members different from the annular member 210. In this case, the wire insertion portions 211 are fixed to the inner surface of the annular member 210 by welding or brazing, not shown. Though not shown, for example, part of the annular member 210 can be pressed and formed integrally with the wire insertion portions 211 as one unit.

As shown in FIGS. 3A, 3B, 4A and 4B, the projection portions of the annular member 220 corresponding to the projection portions 213 and 215 are referred to as projection portions 223 and 225, and the projection portions of the annular member 230 corresponding to the projection portions 213 and 215 are referred to as projection portions 233 and 235. When the projection portions 223, 233 and 235 are viewed from arrow 3A shown in FIGS. 3C and 3D, the projection portions 223, 233 and 235 close to arrow 3A (the projection portions 223, 233 and 235 shown in the upper part of FIGS. 3C and 3D) are indicated by solid lines in FIG. 3A, and the projection portions 223, 233 and 235 far from arrow 3A (the projection portions 223, 233 and 235 shown in the lower part of FIGS. 3C and 3D) are indicated by dotted lines in FIG. 3A. In other words, the projection portions 223, 233 and 235 indicated by the solid lines in FIG. 3A are provided on the upper surface side of the annular member 210 and the projection portions 223, 233 and 235 indicated by the dotted lines in FIG. 3A are provided on the lower surface side of the annular member 210. The projection portions 213, 223 and 233 are different in relative position from one another in a circumferential direction of the second bendable tube 200, the details of which will be described later. Similarly, the projection portions 215, 225 and 235 are different in relative position from one another.

In the following descriptions, the through hole portions of the annular member 220 corresponding to the through hole portions 213a and 215a are referred to as through hole portions 223a and 225a, and the through hole portions of the annular member 230 corresponding to the through hole portions 213a and 215a are referred to as through hole portions 233a and 235a.

In the following descriptions, the wire insertion portion of the annular member 220 corresponding to the wire insertion portion 211 is referred to as a wire insertion portion 221, and the wire insertion portion of the annular member 230 corresponding to the wire insertion portion 211 is referred to as a wire insertion portion 231. The wire insertion portions 211, 221 and 231 are different in relative position from one another in the circumferential direction of the second bendable tube 200, the details of which will be described later.

Next, the connection configuration of the annular members 210, 220 and 230 including the relationship in position among the projection portions 213, 215, 223, 225, 233 and 235 will be described.

[Connection Configuration of Annular Members 220 and 210]

The connection configuration of the annular members 220 and 210 described here is not the connection configuration of the annular members 220 and 210 provided in one bendable tube segment. The connection configuration described here is, for example, the connection configuration of the annular member 210 provided in the first bendable tube segment 410 and the annular member 220 of the second bendable tube segment 420 provided more forward than and adjacent to the first bendable tube segment 410, as shown in FIG. 3A. The connection configuration described here is, for example, the connection configuration of the annular member 220 provided in the first bendable tube segment 410 and the annular member 210 of the third bendable tube segment 430 provided more backward than and adjacent to the first bendable tube segment 410.

Figure 3C:
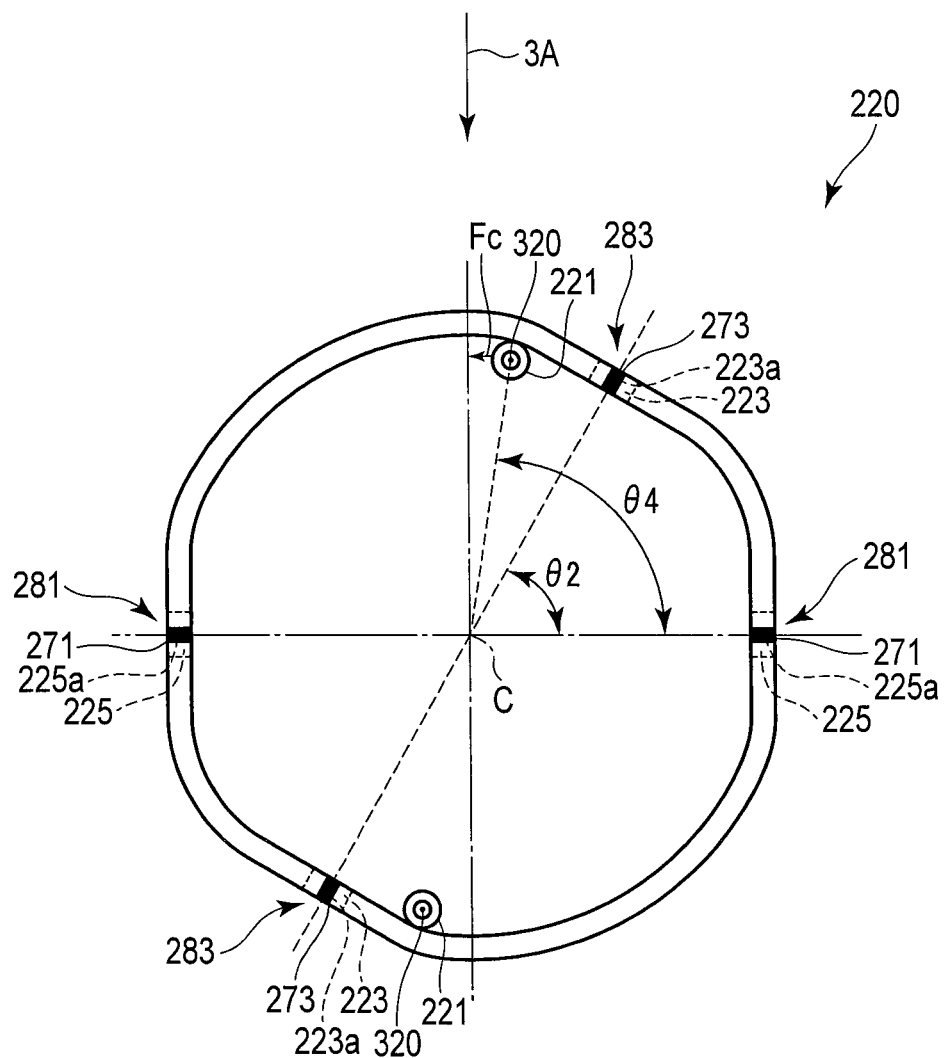
FIG. 3C is a diagram showing a relationship in position between each structural member of a second annular member shown in FIG. 3A and a rotation axis thereof.

As shown in FIGS. 3A, 3B and 3C, the projection portion 225 on the rear side of the annular member 220 is provided in the same position as the projection portion 213 on the front side of the annular member 210 in the circumferential direction.

As shown in FIG. 3A, in the projection portions 225 and 213, for example, the projection portion 213 is stacked on the projection portion 225 in such a manner that the through hole portion 225a communicates with the through hole portion 213a. In this state, as shown in FIGS. 3A, 3B and 3C, a rivet 271 that is a rotation member (axis) is inserted into each of the through hole portions 225a and 213a. Accordingly, the annular members 220 and 210 are connected to each other through the rivet 271 and supported rotatably around the rivet 271 as a center. Between the projection portions 225 and 213, therefore, a support shaft portion which includes the rivet 271 that is a rotation support shaft is formed.

In other words, the projection portions 225 and 213 and rivet 271 function as a connecting portion that connects the annular members 220 and 210. The projection portions 225 and 213 and rivet 271 function as a second up-and-down rotation axis 281 (first rotation axis) of the second bendable tube 200 that bends in an up-and-down direction (first rotation direction). The second up-and-down rotation axis 281 (first rotation axis) is provided along the right-and-left direction on the cross section of the annular members 210 and 220. The projection portions 225 and 213 and rivet 271 are located in, for example, the right-and-left direction of the up-and-left and right-and-left directions on the cross section of the annular members 210 and 220. In FIGS. 3B and 3C, the projection portions 225 and 213, rivet 271 and second up-and-down rotation axis 281 are shown on the right and left sides of the figure. Thus, one of the annular members 210 and 220 rotates around the second up-and-down rotation axis 281 (first rotation axis) as a center with regard to the other annular member in the up-and-down direction orthogonal to the right-and-left direction (second up-and-down rotation axis direction).

As shown in FIGS. 3A and 3B, the paired projection portions 213 are each formed at the distal end portion that is a first one end of the annular member 210. The paired projection portions 213 are opposed to the central axis C of the second bendable tube 200 in the radial direction of the annular member 210. The paired projection portions 213 are a pair of first one-end joint portions which defines the second up-and-down rotation axis 281 that is the rotation axis of the second bendable tube 200.

As shown in FIGS. 3A and 3C, the paired projection portions 225 are each provided at the proximal end portion of the annular member 220 that is a second other end of the annular member 220, which is opposed to a second one end of the annular member 220. The paired projection portions 225 are each provided at the proximal end portion of the annular member 220 that is the second other end of the annular member 220, which is opposed to the first one end in the direction of the central axis of the second bendable tube 200. The paired projection portions 225 are opposed to the central axis C of the second bendable tube 200 in the radial direction of the annular member 220. The paired projection portions 225 are a pair of second other-end joint portions which defines the second up-and-down rotation axis 281 that is the rotation axis of the second bendable tube 200. The second other-end joint portions are connected to the first one-end joint portion and can be rotated around the first one-end joint portion of the annular member 210.

[Connection Configuration of Annular Members 210 and 230]

The connection configuration of the annular members 210 and 230 described here is the connection configuration of the annular members 210 and 230 provided in one bendable tube segment 410 as shown in FIG. 3A.

Figure 3D:
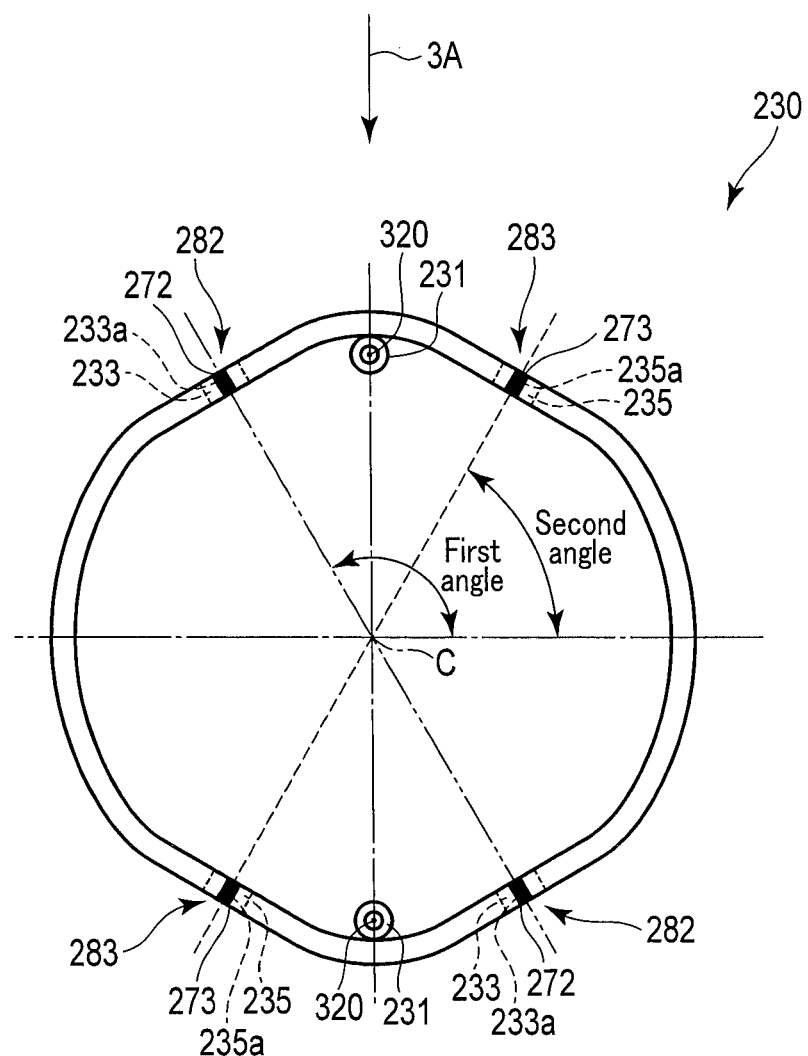
FIG. 3D is a diagram showing a relationship in position between each structural member of a third annular member shown in FIG. 3A and a rotation axis thereof.

As shown in FIGS. 3A, 3B and 3D, the projection portion 215 on the rear side of the annular member 210 is provided in the same position as the projection portion 233 on the front side of the annular member 230 in the circumferential direction. For example, the projection portions 215 and 233 are provided in a position shifted by, e.g. 120 degrees, which is a first angle θ1, counterclockwise on the second up-and-down rotation axis 281 on the cross section of the annular members 210 and 230.

As shown in FIG. 3A, in the projection portions 215 and 233, for example, the projection portion 233 is stacked on the projection portion 215 in such a manner that the through hole portion 215a communicates with the through hole portion 233a. In this state, as shown in FIGS. 3A, 3B and 3D, a rivet 272 that is a rotation member (axis) is inserted into each of the through hole portions 215a and 233a. Accordingly, the annular members 210 and 230 are connected to each other through the rivet 272 and supported rotatably around the rivet 272 as a center. Between the projection portions 215 and 233, therefore, a support shaft portion which includes the rivet 272 that is a rotation support shaft is formed.

In other words, the projection portions 215 and 233 and rivet 272 function as a connecting portion that connects the annular members 210 and 230. The projection portions 215 and 233 and rivet 272 function as a first oblique rotation axis 282 (second rotation axis) of the second bendable tube 200 that bends passively in a first oblique direction (second rotation direction). Thus, one of the annular members 210 and 230 rotates around the first oblique rotation axis 282 (second rotation axis) as a center with regard to the other annular member in the first oblique direction orthogonal to the first oblique rotation axis direction (second rotation axis direction).

As shown in FIGS. 3A and 3B, the paired projection portions 215 are each provided at the proximal end portion of the annular member 210, which is a first other end of the annular member 210, which is opposed to a first one end. The paired projection portions 215 are opposed to the central axis C of the second bendable tube 200 in the radial direction of the annular member 210. The paired projection portions 215 are a pair of first other-end joint portions which are shifted by the first angle θ1 (e.g. 120 degrees), which is an obtuse angle, in the circumferential direction of the second bendable tube 200 with regard to the rotation axis (second up-and-down rotation axis 281) of the second bendable tube 200.

As shown in FIGS. 3A and 3D, the paired projection portions 233 are each provided at the distal end portion of the annular member 230, which is a third one end of the annular member 230, which is opposed to a first one end, in the central axis direction of the second bendable tube 200. The paired projection portions 233 are opposed to the central axis C of the second bendable tube 200 in the radial direction of the annular member 230. The paired projection portions 233 are a pair of third one-end joint portions which are connected to the first other-end joint portion and rotatable around the annular member 210. Like the paired projection portions 215, the paired projection portions 233 are shifted by the first angle θ1 (e.g. 120 degrees), which is the obtuse angle, in the circumferential direction of the second bendable tube 200 with regard to the rotation axis (second up-and-down rotation axis 281) of the second bendable tube 200.

[Connection Configuration of Annular Members 230 and 220]

The connection configuration of the annular members 230 and 220 described here is the connection configuration of the annular members 230 and 220 provided in one bendable tube segment 410 as shown in FIG. 3A.

As shown in FIGS. 3A, 3C and 3D, the projection portion 235 on the rear side of the annular member 230 is provided in the same position as the projection portion 223 on the front side of the annular member 220 in the circumferential direction. For example, the projection portions 235 and 223 are provided in a position shifted by, e.g. 60 degrees, which is a second angle θ2, counterclockwise on the second up-and-down rotation axis 281 and is provided in a position shifted by, e.g. 60 degrees clockwise on the first oblique rotation axis 282 on the cross section of the annular members 230 and 220.

As shown in FIG. 3A, in the projection portions 235 and 223, for example, the projection portion 223 is stacked on the projection portion 235 in such a manner that the through hole portion 235a communicates with the through hole portion 223a. In this state, as shown in FIGS. 3A, 3C and 3D, a rivet 273 that is a rotation member (axis) is inserted into each of the through hole portions 235a and 223a. Accordingly, the annular members 230 and 220 are connected to each other through the rivet 273 and supported rotatably around the rivet 273 as a center. Between the projection portions 235 and 223, therefore, a support shaft portion which includes the rivet 273 that is a rotation support shaft is formed.

In other words, the projection portions 235 and 223 and rivet 273 function as a connecting portion that connects the annular members 230 and 220. The projection portions 235 and 223 and rivet 273 function as a second oblique rotation axis 283 (third rotation axis) of the second bendable tube 200 that bends passively in a second oblique direction (second rotation direction). Thus, one of the annular members 230 and 220 rotates around the second oblique rotation axis 283 (third rotation axis) as a center with regard to the other annular member in the second oblique direction orthogonal to the second oblique rotation axis direction (third rotation axis direction).

As shown in FIGS. 3A and 3C, the paired projection portions 223 are each provided at the distal end portion of the annular member 220 which is a second one end of the annular member 220. The paired projection portions 223 are opposed to the central axis C of the second bendable tube 200 in the radial direction of the annular member 220. The paired projection portions 223 are a pair of second one-end joint portions which are shifted by the second angle θ2 (e.g. 60 degrees), which is an acute angle that differs from the first angle θ1 (e.g. 120 degrees), in the circumferential direction of the second bendable tube 200 that is same as the first angle with regard to the rotation axis (second up-and-down rotation axis 281) of the second bendable tube 200. The projection portion 223 is provided in a position shifted by, e.g. 60 degrees counterclockwise on the second up-and-down rotation axis 281.

As shown in FIGS. 3A and 3D, the paired projection portions 235 are each provided at the proximal end portion of the annular member 230, which is a third other end of the annular member 230, which is opposed to a second one end, in the central axis direction of the second bendable tube 200. The paired projection portions 235 are opposed to the central axis C of the second bendable tube 200 in the radial direction of the annular member 230. The paired projection portions 235 are a pair of third other-end joint portions which are connected to the second one-end joint portion and rotatable around the annular member 220. Like the paired projection portions 223, the paired projection portions 235 are shifted by the second angle θ2 (e.g. 60 degrees), which is an acute angle, in the circumferential direction of the second bendable tube 200 with regard to the rotation axis (second up-and-down rotation axis 281) of the second bendable tube 200.

[Positions of Wire Insertion Portions 211, 231 and 221]

Taking into consideration that the second bendable tube 200 bends actively and passively in the up-and-down direction and bends actively in the first and second oblique directions as in the present embodiment, the second operation wire 320 needs to be provided only in the up-and-down direction orthogonal to the second up-and-down rotation axis 281. Thus, the wire insertion portions 211, 231 and 221 that hold the second operation wire 320 also need to be provided in the up-and-down direction. In this case, the wire insertion portions 211, 231 and 221 are provided on the same straight line, not shown, in the longitudinal direction of the second bendable tube 200.

When the second operation wire 320 is operated in this state, a force is exerted on the wire insertion portions 211, 231 and 221 toward the same direction from the second operation wire 320.

For example, the force is applied to the wire insertion portions 211, 231 and 221 from the second operation wire 320 such that it is separated from the first oblique rotation axis direction and directed toward the first oblique direction. The force is accumulated in the second bendable tube 200 through the wire insertion portions 211, 231 and 221 and thus exerts on the second bendable tube 200. Therefore, there is a case where when the second bendable tube 200 bends actively in a specific direction such as the up-and-down direction, the second bendable tube 200 receives the force and passively bends without intention in the first oblique direction around the first oblique rotation axis direction as a center.

For example, the force is applied to the wire insertion portions 211, 231 and 221 from the second operation wire 320 such that it is separated from the second oblique rotation axis direction and directed toward the second oblique direction. The force is accumulated in the second bendable tube 200 through the wire insertion portions 211, 231 and 221 and thus exerts on the second bendable tube 200. Therefore, there is a case where when the second bendable tube 200 bends actively in the specific direction such as the up-and-down direction, the second bendable tube 200 receives the force and passively bends without intention in the second oblique direction around the second oblique rotation axis direction as a center.

The force applied to the wire insertion portions 211, 231 and 221 from the second operation wire 320 in the same direction becomes greater toward the distal end portion of the second bendable tube 200. The force is also transmitted to the first bendable tube 100 through the second bendable tube 200, with the result that it affects the whole of the bendable tube 23.

As described above, there is a case where when the second bendable tube 200 bends actively in the specific direction such as the up-and-down direction, the second bendable tube 200 bends passively in an unintended direction as the first and second oblique directions. This phenomenon includes a state in which the distal end portion of the bendable tube 23 is directed to an unintended direction, a state in which the bendable tube 23 as a whole is inclined and twisted without intention, and the like. If the phenomenon that the bendable tube bends in an unintended direction appears, the observation field will be shifted when the bendable tube 23 bends.

In the present embodiment, therefore, the second operation wire 320 is provided to prevent the force from being exerted on the second bendable tube 200. As a specific example of disposition of the second operation wire 320, the second operation wire 320 is considered that the second operation wire 320 is provided not linearly but meanderingly in the second bendable tube 200 as shown in FIG. 3A. The wire insertion portions 211, 231 and 221 are formed such that the second operation wire 320 is provided meanderingly.

Therefore, as shown in FIGS. 3A, 3B and 4A, the wire insertion portion 211 is provided to shift by a third angle θ3, which is an obtuse angle smaller than the first angle θ1 (e.g. 120 degrees), in the same direction as the first angle θ1 with regard to the rotation axis (second up-and-down rotation axis 281) of the second bendable tube 200. Thus, the wire insertion portion 211 is provided in a position shifted by, e.g. 90 degrees or larger and 120 degrees or smaller counter-clockwise on the second up-and-down rotation axis 281. The wire insertion portion 211 is provided in a position opposite to the central axis C of the second bendable tube 200 on the inner surface of the annular member 210. In other words, the wire insertion portions 211 are located and opposite to each other at a shifted angle to a straight line which is orthogonal to the second up-and-down rotation axis 281 and passes through the central axis C of the second bendable tube 200 on the inner surface of the annular member 210. This straight line is one indicating the up-and-down direction in FIGS. 3B, 3C and 3D and passing through the wire insertion portion 231.

Figure 4B:
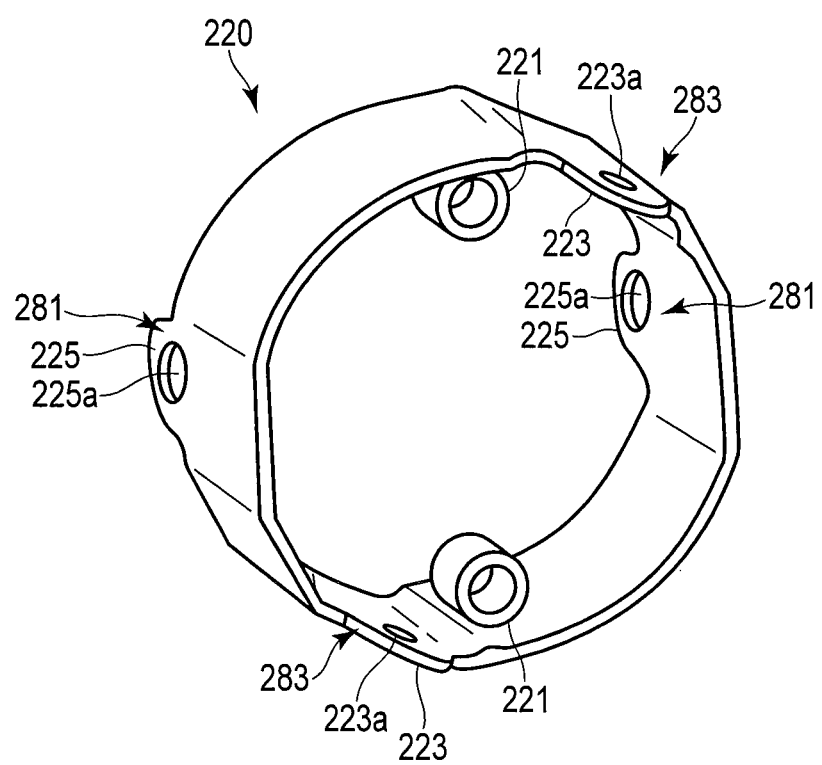
FIG. 4B is a perspective view of the second annular member shown in FIGS. 3A and 3B.

As shown in FIGS. 3A, 3C and 4B, the wire insertion portion 221 is provided to shift by a fourth angle θ4, which is an acute angle larger than the second angle θ2 (e.g. 60 degrees), in the same direction as the second angle θ2 with regard to the rotation axis (second up-and-down rotation axis 281) of the second bendable tube 200. Thus, the wire insertion portion 221 is provided in a position shifted by, e.g. 60 degrees or larger and 90 degrees or smaller counterclockwise on the second up-and-down rotation axis 281. The wire insertion portion 221 is provided in a position opposite to the central axis C of the second bendable tube 200 on the inner surface of the annular member 220. In other words, the wire insertion portions 221 are located and opposite to each other at a shifted angle to the straight line which is orthogonal to the second up-and-down rotation axis 281 and passes through the central axis C of the second bendable tube 200 on the inner surface of the annular member 220. This straight line is one indicating the up-and-down direction in FIGS. 3B, 3C and 3D and passing through the wire insertion portion 231.

More specifically, as shown in FIG. 3A, the wire insertion portions 211, 231 and 221 are located in positions to cause the second operation wire 320 to meander. In other words, the wire insertion portions provided in one annular member is shifted in the circumferential direction from the wire insertion portions provided in the other annular member in such a manner that the wire insertion portions 211, 231 and 221 are provided meanderingly in the longitudinal direction of the second bendable tube 200. The wire insertion portions 211, 231 and 221 are provided to shift from one another in the circumferential direction in such a manner that the central axes of the wire insertion portions 211, 231 and 221 are shifted from one another in the circumferential direction, the wire insertion portions 211, 231 and 221 do not overlap one another in the circumferential direction but provided concentrically. As described above, the wire insertion portions 211, 231 and 221 of the present embodiment are not provided on the straight line in the longitudinal direction of the second bendable tube 200. The wire insertion portion 211 is connected to the annular member 210 and the wire insertion portion 221 is connected to the annular member 220 such that the central axis of the wire insertion portion 211 and that of the second wire insertion portion 221 do not overlap each other in the circumferential direction of the annular members 210 and 220.

As shown in FIGS. 3A and 3B, the wire insertion portion 211 is provided between the projection portion 215 which is the first other-end joint portion, and the orthogonal direction, in the circumferential direction of the second bendable tube 200. The orthogonal direction is a line which is orthogonal to the central axis C of the second bendable tube 200 and the projection portion 213 that is the rotation axis and which passes through the central axis C. The orthogonal direction represents the up-and-down direction in FIGS. 3B, 3C and 3D.

As shown in FIGS. 3A and 3C, the wire insertion portion 221 is provided between the projection portion 223 which is the second one-end joint portion, and the orthogonal direction.

As shown in FIG. 3A, the wire insertion portions 211 and 221 are provided symmetrically each other in the circumferential direction to the orthogonal direction as a center.

As shown in FIGS. 3A and 3D, the wire insertion portion 231 is provided in the orthogonal direction and located opposite to the central axis C of the second bendable tube 200 on the inner surface of the annular member 230.

As described above, as shown in FIGS. 3B, 3C and 3D, the wire insertion portions 211, 231 and 221 are provided between the first and second oblique rotation axes 282 and 283 in the circumferential direction of the second bendable tube 200, and also located in a position at an acute angle between these axes. The wire insertion portion 231 is provided in the up-and-down direction. In other words, the wire insertion portion 231 is provided in a position shifted by, e.g. 90 degrees counterclockwise on the second up-and-down rotation axis 281 on the cross section of the annular member 230. The wire insertion portions 211 and 221 are provided symmetrically to a straight line as a center connecting the wire insertion portion 231 and the central axis C of the second bendable tube 200. In other words, the wire insertion portion 211 is provided on the opposite side of the wire insertion portion 221 around the wire insertion portion 231, in the state which the wire insertion portion 231 is sandwiched between the wire insertion portions 211 and 221 in the circumferential direction of the second bendable tube 200. The wire insertion portions 211 and 221 are separated by, e.g. 10 degrees from the wire insertion portion 231 in the circumferential direction of the second bendable tube 200. Thus, the wire insertion portions 211 and 221 are staggered from each other along the longitudinal direction of the second bendable tube 200 with the wire insertion portion 231 as a center therebetween.

The wire insertion portion 211 is provided between a second up-and-down direction (first rotation direction) which is substantially orthogonal to the direction of the second up-and-down rotation axis 281 (first rotation axis) and a first oblique direction (second rotation direction) which is substantially orthogonal to the direction of the first oblique rotation axis 282 (second rotation axis), and also located in a position at an obtuse angle between these axes. The second operation wire 320 is inserted through each of the paired wire insertion portions 211 such that the second operation wire 320 can move in its axial direction. The wire insertion portion 211 is provided on the inner surface of the annular member 210 to shift at an angle from a straight line orthogonal to each of the rotation axes 281 and 282 on which the annular member 210 rotates. The wire insertion portion 211 is located in a position at a position to form the third angle θ3, which is an obtuse angle, from the second up-and-down rotation axis 281 (first rotation axis).

The wire insertion portion 231 is provided between a first oblique direction (first rotation direction) which is substantially orthogonal to the direction of the first oblique rotation axis 282 (second rotation axis) and a second oblique direction (third rotation direction) which is substantially orthogonal to the direction of the second oblique rotation axis 283 (third rotation axis), and also located in a position at an obtuse angle between these axes. The second operation wire 320 is inserted through each of the paired wire insertion portions 231 such that the second operation wire 320 can move in its axial direction. The wire insertion portion 231 is provided on the inner surface of the annular member 230 to shift at an angle from a straight line orthogonal to each of the rotation axes 282 and 283 on which the annular member 230 rotates.

The wire insertion portion 221 is provided between a second oblique direction (third rotation direction) which is substantially orthogonal to the direction of the second oblique rotation axis 283 (third rotation axis) and a second up-and-down direction (first rotation direction) which is substantially orthogonal to the direction of the second up-and-down rotation axis 281 (first rotation axis), and also located in a position at an obtuse angle between these axes. The second operation wire 320 is inserted through each of the paired wire insertion portions 221 such that the second operation wire 320 can move in its axial direction. The wire insertion portion 221 is provided on the inner surface of the annular member 220 to shift at an angle from a straight line orthogonal to each of the rotation axes 281 and 283 on which the annular member 220 rotates. The wire insertion portion 221 is located in a position at a position to form the fourth angle θ4, which is an obtuse angle, from the second up-and-down rotation axis 281 (first rotation axis).

The connection configuration, the arrangement positions of wire insertion portions 211, 231 and 221 and the second operation wire 320 as described above allow the second bendable tube 200 to be bent actively and passively in the up-and-down direction. The wire insertion portions 211, 231 and 221 are provided meanderingly. Thus, when the second bendable tube 200 bends actively in the specific direction such as the up-and-down direction, it can be prevented from bending passively in the first and second oblique directions.

[Operation]

When the second operation knob 37b is operated, the second operation wire 320 is operated. Accordingly, one of the annular members 210 and 220 rotates in the up-and-down direction around the second up-and-down rotation axis 281 as a center in relative to the other annular member. Thus, the second bendable tube 200 bends actively in the up-and-down direction.

Assuming that the insertion portion 20 is inserted into the body cavity and, for example, the second bendable tube 200 receives an external force from an outside, such as a body wall, one of the annular members 210 and 220 rotates passively in the up-and-down direction around the second up-and-down rotation axis 281 as a center in relative to the other annular member. One of the annular members 210 and 230 rotates passively in the first oblique direction around the first oblique rotation axis 282 as a center in relative to the other annular member. One of the annular members 230 and 220 rotates passively in the second oblique direction around the second oblique rotation axis 283 as a center in relative to the other annular member. Thus, the second bendable tube 200 bends passively in the up-and-down direction, first oblique direction and second oblique direction.

In the foregoing descriptions, when the second bendable tube 200 bends actively in the up-and-down direction, in the annular member 210, as shown in, for example, FIG. 3B, a force Fa applied from the second operation wire 320 to the wire insertion portion 211 is separated from the first oblique rotation axis direction and directed to the first oblique direction. In the annular member 220, as shown in, for example, FIG. 3C, a force Fc applied from the second operation wire 320 to the wire insertion portion 221 is separated from the second oblique rotation axis direction and directed to the second oblique direction.

As described above, when the force Fa and force Fc are generated, a direction of the force Fa and a direction of the force Fc are opposed to each other, and the force Fa and the force Fc are canceled each other. Thus, the force applied from the second operation wire 320 to each of the wire insertion portions is prevented from being accumulated in the second bendable tube 200, and the force is prevented from exerting on the second bendable tube 200. Therefore, when the second bendable tube 200 bends actively in the specific direction such as the up-and-down direction, the second bendable tube 200 is prevented from bending passively in the first and second oblique directions without intention upon receipt of the force.

As a result, the force applied from the second operation wire 320 to each of the wire insertion portions is prevented from being transmitted to the first bendable tube 100 through the second bendable tube 200, and the force is prevented from affecting the whole of the bendable tube 23.

As described above, the wire insertion portions 211, 221 and 231 are provided meanderingly and accordingly the second operation wire 320 is also provided meanderingly. Therefore, even though the forces are applied from the second operation wire 320 to the wire insertion portions, the forces are canceled each other and thus prevented from exerting on the second bendable tube 200

Therefore, when the second bendable tube 200 bends actively in the specific direction such as the up-and-down direction, the second bendable tube 200 is prevented from bending passively in an unintended direction such as the first and second oblique directions.

As described above, in the present embodiment, the insertion portion 20 is inserted into the body cavity and, for example, the second bendable tube 200 receives the external force from the outside, such as the body wall, the second bendable tube 200 bends passively in the first and second oblique directions. When the second bendable tube 200 bends actively in the specific direction such as the up-and-down direction, it is prevented from bending passively in the first and second oblique directions according to bending actively.

Advantages

In the present embodiment, the wire insertion portions 211, 231 and 221 are provided meanderingly, thus, even though the forces are generated, they are canceled each other; accordingly, the forces are prevented from exerting on the second bendable tube 200. In the present embodiment, therefore, when the bendable tube 23, which can be bent passively, bends actively in the specific direction, it can be prevented from bending passively in an unintended direction.

In the present embodiment, the wire insertion portions 211 and 221 are provided symmetrically each other. In the present embodiment, therefore, the second operation wire 320 can be provided meanderingly with reliability and the forces can be canceled with reliability, with the result that the foregoing can be achieved.

In the present embodiment, the wire insertion portion 231 is provided to prevent the second operation wire 320 that is provided meanderingly from shifting in position.

In the present embodiment, the second bendable tube 200 can be bent in six directions. In the present embodiment, therefore, it can be bent relatively finely in a desired direction.

Furthermore, the wire insertion portion 211 can be shaped by cutting and bending part of the peripheral wall portion of the annular member 210 from the outer surface toward the inner surface by pressing and then projecting and raising the part. This shaping is true of the wire insertion portions 221 and 231.

In the foregoing descriptions, the bendable tube segment has only to include at least the annular members 210 and 220. The annular members 210, 230 and 220 can be provided in opposite order and, in other words, the annular members 220, 230 and 210 can be provided in the order presented.

In the bendable tube segment provided at the most distal end, the annular member 210 can be excluded. In this case, the first mouthpiece portion 301 that is an annular member functions as the annular member 210, and the annular member 230 has only to be connected to the first mouthpiece portion 301. Or the annular members 210 and 230 can be excluded and, in this case, the first mouthpiece portion 301 functions as the annular member 210, and the annular member 220 has only to be connected to the first mouthpiece portion 301.

In the bendable tube segment provided at the most proximal end, the annular member 220 can be excluded. In this case, the second mouthpiece portion 302 that is an annular member functions as the annular member 220, and the annular member 230 has only to be connected to the second mouthpiece portion 302. Or the annular members 230 and 220 can be excluded and, in this case, the second mouthpiece portion 302 functions as the annular member 220, and the annular member 210 has only to be connected to the second mouthpiece portion 302.

The second bendable tube 200 has only to include at least one bendable tube segment as described above.

It is favorable that the wire insertion portions 211, 231 and 221 are provided at regular intervals in the longitudinal direction of the second bendable tube 200. It is favorable that the wire insertion portion 211 is formed in the center of the annular member 210 in the longitudinal direction of the annular member 210. This relationship in disposition is true of a set of the wire insertion portion 231 and annular member 230 and a set of the wire insertion portion 221 and annular member 220.

In the present embodiment, if the second operation wire 320 is provided meanderingly, the wire insertion portion 231 can be excluded. In the present embodiment, therefore, the internal space of the annular member 230 can be secured.

According to the present embodiment, in the second bendable tube 200, the positions of the wire insertion portions 211, 231 and 221 in the central axis direction of the annular members 210, 230 and 220 may differ from one another. For example, the wire insertion portion 211 can be provided on the distal end side of the annular member 210, and the wire insertion portion 221 can be provided on the proximal end side of the annular member 220. Thus, when the second operation wire 320 meanders, the curvature of the meander can be adjusted to a desired value, and the length of the second operation wire 320 can be adjusted to a desired value.

In the present embodiment, the lengths of the annular members 210, 230 and 220 in the direction of the central axis C of the second bendable tube 200 may differ from one another. For example, the annular member 210 provided on the distal end side of the second bendable tube 200 is short, and the annular member 210 provided on the proximal end side of the second bendable tube 200 is long. Thus, when the second operation wire 320 meanders, it can be prevented from meandering suddenly and thus meander slowly. In other words, the curvature of the meander can be increased, and the second operation wire 320 can be shortened. At the time of operation, when the second operation wire 320 slides the wire insertion portions 211, 231 and 221, it can be prevented from being worn.

The first bendable tube 100 can be bent actively in the right-and-left direction, too. In this case, the bendable operation portion has only to include a third operation knob to bend the first bendable tube 100 right and left, for example, and an additional third operation wire has only to be provided.

The present invention is not limited to the foregoing embodiment as it is. When the invention is reduced to practice, its structural elements can be modified and embodied without departing from the spirit of the invention. A variety of inventions can be made by appropriate combinations of the structural elements of the embodiment.

What is claimed is:

1. A bendable tube which is bendable and having a central axis extending in a longitudinal direction, comprising:
   a first annular member having one end and an other end;
   a second annular member having one end and an other end;
   a third annular member provided between the first annular member and the second annular member, the third annular member having one end adjacent to the other end of the first annular member and the third annular member having an other end adjacent to the one end of the second annular member;
   a first rotation axis provided at the one end of the first annular member, the first rotation axis being a center around which the first annular member rotates;
   a second rotation axis which hingedly connects the first annular member and the third annular member, the second rotation axis being a center around which the first annular member and the third annular member rotate each other, the second rotation axis being provided at an angle different from the first rotation axis with regard to the central axis;
   a third rotation axis which hingedly connects the second annular member and the third annular member, the third rotation axis being a center around which the second annular member and the third annular member rotate each other, the third rotation axis being provided at an angle different from the first and second rotation axes with regard to the central axis;
   a first wire insertion portion fixed to an inner surface of the first annular member, and through which an operation wire is inserted; and
   a second wire insertion portion fixed to an inner surface of the second annular member, and through which the operation wire is inserted, the second wire insertion portion being shifted in a circumferential direction with respect to the first wire insertion portion;
   wherein the first wire insertion portion and the second wire insertion portion are configured such that:
   when the operation wire is pulled, the first wire insertion portion is configured to receive a first force along a first circumferential direction of the first annular member by the operation wire, and the second wire insertion portion is configured to receive a second force along a second circumferential direction of the second annular member by the operation wire; and
   when the first wire insertion portion receives the first force and the second wire insertion portion receives the second force, the first circumferential direction of the first force and the second circumferential direction of the second force are opposed to each other, and the first wire insertion portion and the second wire insertion portion are at positions where the first force and the second force cancel each other.

2. The bendable tube according to claim 1, wherein the first wire insertion portion is connected to the first annular member and the second wire insertion portion is connected to the second annular member such that a central axis of the first wire insertion portion and a central axis of the second wire insertion portion do not overlap each other in a circumferential direction of the first annular member and the second annular member.

3. The bendable tube according to claim 1, wherein:
   the second rotation axis is provided to shift by a first angle, which is an obtuse angle, in one direction of the circumferential direction of the first annular member from a straight line orthogonal to the central axis and the first rotation axis; and
   the third rotation axis is provided to shift by a second angle, which is an acute angle different from the first angle, in the one direction of the circumferential direction from the first rotation axis.

4. The bendable tube according to claim 3, wherein the first angle is 120 degrees, and the second angle is 60 degrees.

5. The bendable tube according to claim 1, wherein the third annular member includes a third wire insertion portion through which the operation wire is inserted and which is provided on an inner surface of the third annular member to shift at an angle in a circumferential direction of the third annular member from a straight line orthogonal to each of the second rotation axis and the third rotation axis.

6. The bendable tube according to claim 1, wherein, when viewed along a direction perpendicular to the central axis:
   the first wire insertion portion is shifted by a predetermined angle in a first direction of the circumferential direction with respect to the first rotation axis; and
   the second wire insertion portion is shifted by a predetermined angle in a second direction of the circumferential direction different from the first direction with respect to the first rotation axis.

7. The bendable tube according to claim 6, wherein:
   the first wire insertion portion is located at a position to form a third angle, which is an obtuse angle, from the first rotation axis; and the second wire insertion portion is located at a position to form a fourth angle, which is an acute angle, from the first rotation axis.

8. A bendable tube comprising:
a first bendable tube which is provided on a distal end side of central axis and which is bendable by connecting a plurality of annular members by a plurality of joint portions including the rotation axis orthogonal to the central axis; and
the bendable tube according to claim 1 which functions as a second bendable tube provided on a proximal end side of the first bendable tube in the central axis.

9. An insertion device comprising an insertion portion including the bendable tube according to claim 1.

10. The bendable tube according to claim 1, wherein:
the first wire insertion portion includes a pair of first wire insertion portions;
one of the pair of first wire insertion portions is provided in a position shifted in one direction of a circumferential direction of the first annular member from a straight line orthogonal to the central axis and the first rotation axis; and
an other of the pair of first wire insertion portions and the one of the pair of first wire insertion portions are each provided in a position symmetrically with regard to the central axis as a center.

11. The bendable tube according to claim 10, wherein:
the second wire insertion portion includes a pair of second wire insertion portions;
one of the pair of second wire insertion portions is provided in a position shifted in an other direction from the straight line and provided to shift from the one of the first wire insertion portions in the circumferential direction; and
an other of the pair of second wire insertion portions and the one of the pair of second wire insertion portions are each provided in a position symmetrically with regard to the central axis as a center.

12. The bendable tube according to claim 1, wherein:
the first wire insertion portion is arranged at a position shifted from an axis, which is orthogonal to the central axis and the center of the first annular member, by a predetermined angle in an counterclockwise direction, and
the second wire insertion portion is arranged at a position shifted from the axis, which is orthogonal to the central axis and the center of the first annular member, by an angle identical to the predetermined angle in a clockwise direction.

* * * * *